United States Patent
Brasch et al.

(10) Patent No.: US 6,312,664 B1
(45) Date of Patent: *Nov. 6, 2001

(54) BIODEGRADABLE CONTRAST MEDIA FOR MR IMAGING

(75) Inventors: Robert C. Brasch, Mill Valley; Jeffry S. Mann, San Francisco; Danute E. Nitecki, Berkeley, all of CA (US)

(73) Assignee: The Regents of the University of California, Oakland, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/096,645

(22) Filed: Jun. 12, 1998

Related U.S. Application Data

(60) Division of application No. 08/446,591, filed as application No. PCT/US94/00597 on May 19, 1994, now Pat. No. 5,811,076, which is a continuation-in-part of application No. 08/064,628, filed on May 20, 1993, now abandoned.

(51) Int. Cl.⁷ .............................. A61B 5/055; C07F 5/00
(52) U.S. Cl. ................. 424/9.35; 424/9.363; 424/9.364; 424/9.4; 534/15
(58) Field of Search .............................. 424/9.363, 9.364, 424/9.34, 9.35; 534/15; 556/50, 63, 107, 117, 134, 148; 600/420; 530/300; 536/1.11

(56) References Cited

U.S. PATENT DOCUMENTS

| | | | |
|---|---|---|---|
| 4,647,447 | 3/1987 | Gries et al. | 424/9.36 |
| 5,208,324 | 5/1993 | Klaveness et al. | 534/16 |
| 5,346,687 | 9/1994 | Rhodes . | |
| 5,364,614 * | 11/1994 | Platzek et al. | 424/9 |
| 5,505,932 * | 4/1996 | Grinstaff et al. | 424/9.3 |
| 5,517,993 * | 5/1996 | Unger et al. | 600/420 |
| 5,650,133 * | 7/1997 | Carbalho et al. | 424/1.65 |
| 5,756,069 * | 5/1998 | Torchilin et al. | 424/9.321 |
| 5,801,228 * | 9/1998 | Hollister et al. | 534/15 |
| 5,817,292 * | 10/1998 | Snow et al. | 424/9.323 |
| 5,817,774 * | 10/1998 | Delecki et al. | 534/10 |
| 5,871,710 * | 2/1999 | Bogdanov et al. | 424/1.65 |

FOREIGN PATENT DOCUMENTS

| | | |
|---|---|---|
| 3806795 A1 | 9/1989 | (DE) . |
| 0629617A1 | 12/1994 | (EP) . |
| WO 85/05554 | 12/1985 | (GB) . |
| WO 89/01476 | 2/1989 | (GB) . |
| WO93/06148 | 4/1993 | (WO) . |
| WO94/05203 | 3/1994 | (WO) . |
| 96/00588 * | 1/1996 | (WO) . |

OTHER PUBLICATIONS

Chemical Abstracts, vol. 112, Issued Sep. 1, 1989, Deutsch et al., "Polymer bonded complexing agents and their complexes for use in pharmaceuticals", abstract No. 140,769, DE 3,806,795.

* cited by examiner

*Primary Examiner*—Michael G. Hartley
(74) *Attorney, Agent, or Firm*—Townsend and Townsend and Crew LLP

(57) ABSTRACT

A macromolecular contrast agent for magnetic resonance imaging of the vascular system is constructed of a polymeric backbone structure with a plurality of spacer arms bonded to the backbone structure, each spacer arm terminating in at least one paramagnetic complex. The polymeric backbone thus serves as an amplifier by supporting a multitude of paramagnetic complexes, and the spacer arms contribute to the molecular weight. The spacer arms further contribute useful properties to the agent, such as hydrophilicity and the ability to cleave at a relatively rapid rate in blood.

31 Claims, No Drawings

BIODEGRADABLE CONTRAST MEDIA FOR MR IMAGING

CROSS REFERENCE TO RELATED APPLICATIONS

This application is a division of U.S. Ser. No. 08/446,591, filed Jul. 28, 1995, which is a 371 of PCT/US94/00597,filed May 19, 1994, now U.S. Pat. No. 5,811,076, which is a Continuation-In-Part of U.S. Ser. No. 08/064,628, filed May 20, 1993, now abandoned, the contents of which are incorporated herein by reference.

This invention was made at least in part with United States Government support under Grant No. R01 CA49786-02, awarded by the National Cancer Institute of the National Institutes of Health. The United States Government has certain rights in this invention.

This invention resides in the field of contrast media for magnetic resonance imaging in medical procedures.

BACKGROUND OF THE INVENTION

Magnetic resonance (MR) imaging is a developing field with ever-expanding applications. Much of this expansion is attributable to the development of a wide array of contrast agents, which increase the contrast of the image by modifying localized areas of the contrast in either a positive or negative maiser. The regions of localization vary considerably among the various types of contrast agents. These regions include specific tissues, organs, cells, antigens, and tumors, as well as the blood pool itself.

Of interest in the present invention are contrast agents used for imaging the blood pool and monitoring its movement. MR imaging assisted by such agents is useful for such procedures as assessments of relative tissue blood volume, estimation of tissue per fusion, and detection of abnormal capillary permeability. Clinical applications include assessments of myocardial and cerebral ischemia, pulmonary embolism, transplants, and neoplasia. To be useful as blood-pool markers, the contrast agents must remain in the pool rather than leaving it through such means as diffusion into extravascular compartments or glomerular filtration. A requisite property of contrast agents is therefore a relatively high molecular weight, generally on the order of 20,000 daltons or more, which prevents the agents from diffusing through normal capillaries and glomerular endothelium. Contrast agents of this type are thus referred to in the art as macromolecular contrast media, or "MMCM." A further advantage of MMCM is that the prolonged intravascular retention of these agents permits imaging of the blood pool in multiple body regions without repeated dosing, thereby eliminating the need for critical timing of the imaging. The enhancement of normal tissues with MMCM 5 minutes after administration, for example, is virtually identical to the enhancement 50 minutes after administration.

SUMMARY OF THE INVENTION

This invention resides in a novel class of MMCM constructs which include a plurality of paramagnetic complexes joined to a macromolecular or polymeric backbone through spacer groups. In prior art MMCM in which most of the high molecular weight resides in the polymeric backbone, the MMCM are generally polydisperse in molecular weight due to the polydispersity of the backbone. The spacer groups of the present invention provide a means of adding molecular weight to the construct in a manner which permits control of the molecular weight within a narrow range. In addition, the spacer groups offer an opportunity for adding to or modifying the physical and chemical characteristics of the construct. Still further, they provide additional functional groups for the attachment of paramagnetic complexes, thereby further amplifying the signal enhancement within a given molecular weight range.

The constructs of the invention have the following general formula:

The symbol $R^1$ in this formula represents a multifunctional group or backbone providing a multitude of attachment sites for spacer groups. Polymers, including polypeptides, polysaccharides and others, are generally useful for this backbone. With its multitude of attachment sites, the backbone serves an amplifying function for the paramagnetic complexes.

The symbols $R^2$ and $R^3$ represent a spacer group and a paramagnetic complex, respectively, or the spacer group and a ligand which retains the paramagnetic metal cation and thus forms part of the paramagnetic complex. The symbol in represents the number of paramagnetic complexes attached to each spacer. This may be as low as 1, or greater. The symbol n represents the number of spacers, and their associated complexes, which are attached to the backbone, and this will generally be a number in excess of 1, preferably well in excess of 1. The term "ligand" will be used herein for $R^3$ for purposes of convenience, but will refer to both the ligands which combine with the paramagnetic metal cations to form the paramagnetic complexes, and to the complexes themselves.

The spacer $R^2$ can be any of a wide variety of molecular structures, and will be at least bifunctional to permit attachment to both $R^1$ and $R^3$, optionally through linkage groups. Preferred spacers are those which are cleaved in vivo by the biological environment within a relatively short period of time. Spacers with multiple binding functionalities at the complex end (i.e., the $R^3$ end) will accommodate a multitude of complexes, in which case m will have a value exceeding 1. Spacers of this type serve an amplifying function in a manner similar to that of the backbone, although to a lesser extent. Other spacers useful in the invention will have only a single functionality at either end, in which case the value of m will be 1. Useful spacers will be those which are non-toxic and non-immunogenic, while those which are particularly useful will be those which have further properties which benefit the construct when administered as MMCM. In addition to the property of in vivo cleavability mentioned above, a property of prominent interest is hydrophilicity. Still other useful properties are the ability to lower antigenicity and to increase molecular weight. Spacers with still further properties can be utilized to advantage as well, as will be readily apparent to those skilled in the art.

The ligands represented by $R^3$ include any ligand useful as an MR imaging contrast enhancement agent which can be attached to a spacer. These include known ligands which have been modified or derivatized in any of a variety of ways to achieve a functional group which will permit attachment to the spacer.

Further features and advantages of the invention will become apparent from the description which follows.

DETAILED DESCRIPTION OF THE INVENTION AND PREFERRED EMBODIMENTS

Referring to Formula I above, pharmaceutical agents of the present invention are those in which:

$R^1$ is a polymeric backbone group which is non-toxic and non-antigenic;

$R^2$ is a group which includes at least four atoms bonded together and adjoining $R^1$ to $R^3$;

$R^3$ is a complex of a ligand and a paramagnetic metal cation capable of altering contrast in magnetic resonance imaging;

n is at least 3; and m is at least 1.

The spacer $R^2$ may be either a straight-chain or a branched-chain structure. Preferred $R^2$ groups are those which include a straight chain within their structures, either as the entire spacer group or as the backbone of a branched-chain group. The straight chain may be a chain of carbon atoms or of carbon atoms interrupted with one or more hetero atoms such as oxygen atoms, sulfur atoms or nitrogen atoms. The bonds forming the chain may be single bonds or double bonds, although single bonds are preferred. The length of the chain is not critical and may vary widely, depending on the desired relationship between the molecular weight of the construct and the number of paramagnetic groups included on the construct. Best results will generally be obtained with chain lengths ranging from 4 atoms to 1,000 atoms, with preferred chains being those of 6 atoms to 100 atoms, and the most preferred being those of from 10 atoms to 50 atoms. The chain as thus described is the backbone of the spacer itself, and does not include atoms, groups or side chains bonded to the serially bonded atoms forming the backbone. It does however include linking groups at the chain termini joining the chain to $R^1$ and $R^3$, when such linking groups are present.

In certain embodiments of the invention, the spacer will be hydrophilic in character to impart hydrophilicity to the construct. The spacer may thus be any hydrophilic group among those known in the art. Examples are polyalkylene glycols, optionally substituted with groups which may or may not add to their hydrophilic character. Among polyalkylene glycols, polyethylene glycol is a preferred example. Examples of the optional substitutions are alkyl groups, alkoxy groups and hydroxy groups. Unsubstituted polyethylene glycol is particularly preferred. The length of the optionally substituted polyalkylene glycol is not critical and may vary. Selection of the length will be governed by such considerations as achieving the desired molecular weight for the construct and imparting the desired degree of hydrophilic character. In most applications, polyalkylenes having molecular weights ranging from about 100 daltons to about 20,000 daltons will provide the best results, with a range of from about 200 daltons to about 1,000 daltons preferred.

In embodiments of the invention in which the spacer provides in vivo cleavability to the construct, the spacer may contain any of a variety of groups as part of its chain which will cleave in the blood stream at a rate which is enhanced relative to that of constructs which lack such groups. Accelerated rates of cleavage enhance the rates of removal of the potentially toxic paramagnetic ions from the body, and therefore lower the toxicity. Accelerated cleavage rates further permit the administration of higher concentrations of the paramagnetic ions, thereby increasing the MR image contrast. While the degree of cleavage rate enhancement is not critical to the invention, preferred examples of these spacers are those in which at least about 10% of the cleavable groups are cleaved in the blood stream within 24 hours of administration, most preferably at least about 35%. Preferred cleavable groups are ester linkages and disulfide linkages.

In further embodiments of the invention, the spacer both imparts a hydrophilic character to the construct and includes a cleavable group as referred to above.

Structural formulas for the spacer vary widely. One group of structural formulas for spacers which impart a hydrophilic character to the construct are those in which m of Formula I above is 1, and $R^2$ of Formula I is represented by either of Formulas II, III or IV below:

$$X—R^4—Y—R^5—Z \quad \text{(II)}$$

$$X—R^5—Y—R^4—Z \quad \text{(III)}$$

$$X—R^4—Z \quad \text{(IV)}$$

In each of these formulas, the hydrophilic component is represented by $R^4$, which is a polyethylene glycol group having a formula weight of about 100 daltons to about 20,000 daltons, preferably from about 200 daltons to about 1,000 daltons.

In Formulas II and III, the group $R^5$ represents a cleavable group which increases the rate of cleavage of the construct in blood. The group is either a disulfide group S—S, or an ester group oriented in either direction, i.e., C(O)—O or O—(O). Upon cleavage of constructs in which $R^2$ (of Formula I) is represented by Formula II, the polyethylene glycol group will remain with the polymeric backbone $R^1$ (Formula I). Conversely, upon cleavage of constructs in which $R^2$ (Formula I) is represented by Formula III, the polyethylene glycol group will remain with the paramagnetic complex.

The symbols X, Y and Z represent inert linking groups which serve to join the R-groups together. The nature of these linking groups is not critical, and their selection will be largely a matter of convenience as determined by the means of synthesis of the construct. The term "inert" in this context means essentially non-toxic, non-immunogenic, and stable with respect to cleavage or dissociation over the typical period of time required for use of the construct in a clinical or diagnostic procedure. Examples of inert linking groups useful for this purpose are alkylamino or aminoalkyl groups such as $(CH_2)_q$—NH and NH—$(CH_2)_q$, carbamoyl groups such as NH—C(O)—O and O—C(O)—NH, and alkylcarbamoyl or carbanoylalkyl groups such as $(CH_2)_q$—NH—C(O)—O and O—C(O)—NH—$(CH_2)_q$. The symbol q in these groups may vary, but in most cases will generally range from 1 to 10, with 2 to 4 preferred, and 2 particularly preferred. In the context of this invention, these groups may be defined such that terminal atoms in X or Z may be native to $R^1$ or $R^3$, respectively. For example, a terminal NH group in the definition of X or Z may be formed from an amino functional group on $R^1$ or $R^3$ or other N-bearing group which can react to form the NH of the linking group. The same is true of a terminal O atom.

Examples of structures defined by Formula II are as follows:

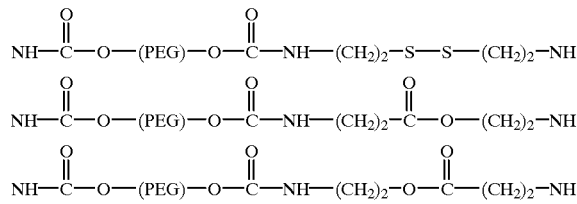

Examples of structures defined by Formula III are as follows:

$$\text{NH—(CH}_2)_2\text{—S—S—(CH}_2)_2\text{—NH—}\overset{\text{O}}{\underset{\|}{\text{C}}}\text{—O—(PEG)—O—}\overset{\text{O}}{\underset{\|}{\text{C}}}\text{—NH}$$

$$\text{NH—(CH}_2)_2\text{—}\overset{\text{O}}{\underset{\|}{\text{C}}}\text{—O—(CH}_2)_2\text{—NH—}\overset{\text{O}}{\underset{\|}{\text{C}}}\text{—O—(PEG)—O—}\overset{\text{O}}{\underset{\|}{\text{C}}}\text{—NH}$$

$$\text{NH—(CH}_2)_2\text{—O—}\overset{\text{O}}{\underset{\|}{\text{C}}}\text{—(CH}_2)_2\text{—NH—}\overset{\text{O}}{\underset{\|}{\text{C}}}\text{—O—(PEG)—O—}\overset{\text{O}}{\underset{\|}{\text{C}}}\text{—NH}$$

In each of the above six structures, the sympol "PEG" refers to a polyethylene glycol segment with terminal hydroxyl groups removed, thereby terminating in ethylene groups at both ends.

As a variation of Formula II, a structural formula for a spacer which supports two or more paramagnetic complexes is represented by Formula V:

$$X\text{—}R^4\text{—}Y'(\text{—}R^5\text{—}Z)_r \quad (V)$$

In this formula, $R^4$, $R^5$, and X are as defined above, with Z restricted to $(CH_2)_q$—NH. The symbol Y' represents a group of the formula $$O\text{—}C(O)\text{—}NH\text{—}(CH_2)_q\text{—}CH_3 \quad (VI)$$

in which q is 1 to 3, and two or more of the H atoms bonded to the C atoms in the $(CH_2)_q$—$CH_3$ portion of the formula are replaced by the substituent NH—$(CH_2)_s$—NH where s is 2 to 4, the number of such substituents being equal to m of Formula 1 such that m is 2 or greater. The result is that the spacer is a branched structure containing two or more functional NH groups for attachment of paramagnetic complexes.

The symbol r of Formula V is either zero or a number equal to m. When r is zero, the spacer lacks a cleavable group, whereas when r is other than zero, a cleavable group is included for each functional NH group on the Z linker to which a paramagnetic complex is attached.

In preferred examples of Formula VI, m is 2 to 6, and in most preferred examples m is 2 or 3.

As a further variation, the terminal $CH_3$ of Formula VI may be replaced by OH or SH. This results in a functional OH or SH group available for the attachment of paramagnetic species.

A further group of structural formulas for $R^2$ of Formula I is that defined by Formula VII:

$$X'\text{—}R^6\text{—}Z' \quad (VII)$$

In Formula VII, $R^6$ is a group having the formula $$(CH_2)_t\text{—}R^7\text{—}(CH_2)_u \quad (VIII)$$

in which $R^7$ a cleavable group bearing the same definition as $R^5$ of Formulas II and III above, i.e., either a disulfide group S—S, or an ester group oriented in either direction, i.e., C(O)—O or O—C(O). The indexes t and u are the same or different and are either zero or a positive integer, such that the sum of t+u is at least 2.

The symbols X' and Y' in Formula VI are the same or different and are inert linking groups of scope similar to the inert linking groups of the previous formulas. Preferred examples of X' and Y' are NH—C(O), C(O)—NH, NH—C(S) and C(S)—NH.

In accordance with these various formulas, the number and arrangement of paramagnetic complexes on a single construct of Formula I may vary considerably. The number of complexes will equal the product of m×n. In general, preferred constructs will be those in which this product is at least 10. More preferred are those in which the product is from 10 to 1,000, and the most preferred are those in which the product is from 30 to 300.

The group $R^1$ of Formula I represents a polymeric group which is non-toxic and at most minimally antigenic and sufficiently functionalized to permit attachment to a multitude of spacer groups, through linkages (preferably cleavable) where appropriate. Examples are poly(amino acids), polysaccharides, derivatized analogs of these groups of compounds, and polymers in general. The term "polymer" is used herein to include oligomers. More narrowly defined classes include linear polypeptides and oligopeptides of both essential and nonessential amino acids, including lysine, ornithine and glutamic acid, for example, and any other polypeptides and oligopeptides which have one or more terminal amino groups and are available in the desired molecular weights in narrow ranges. A further class is that of branched synthetic oligopeptides and polypeptides, such as branched dendrimers of amino acids such as lysine, the dendrimers being readily synthesized in a controlled manner using conventional techniques to yield a controlled number of functional groups. Polysaccharides such as dextrans, starches, and celluloses are a still further class, and simple non-biological polymers such as polyethyleneimine are yet a further class. Derivatized analogs of the polymers of these classes include the polymers modified to contain selected functional groups to permit formation of the linker groups referred to above. An example is poly(aminopropyl)dextran.

A wide variety of paramagnetic complexes may be used as group $R^3$ in Formula I. Preferred complexes are chelates of a paramagnetic metal cation and a chelating agent. Chelates with high thermodynamic and kinetic stabilities are preferred since their ability to remain stable in vivo offers a distinct benefit to MR imaging and to the constructs of the present invention. Macrocyclic chelating ligands are particularly preferred due to their high thermodynamic stability constants and low dissociation rate constants. The ligands must be bifunctional to permit both chelation with the paramagnetic metal cation and attachment to the spacer $R^2$ of the construct, optionally through a linker group as appropriate. While a wide variety of ligands meets this description, a prominent example is 1,4,7,10-tetraazacyclododecane-N,N',N",N"'-tetraacetic acid (DOTA). Further examples are 1,4,7,10-tetraazacyclododecane-N,N',N"-triacetic acid (DO3A), diethylene-triaminepentaacetic acid (DTPA) and various analogs and derivatives of both ligands.

Paramagnetic metals of a wide range are suitable for complexation with these ligands. Suitable metals are those having atomic numbers of 22–29 (inclusive), 42, 44 and 58–70 (inclusive), and have oxidations states of 2 or 3. Those having atomic numbers of 22–29 (inclusive) and 58–70 (inclusive) are preferred, and those having atomic numbers of 24–29 (inclusive) and 64–68 (inclusive) are more preferred. Examples of such metals are chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III) and ytterbium (III). Chromium (III), manganese (II), iron (III) and gadolinium (III) are particularly preferred, with gadolinium (III) the most preferred.

Constructs in accordance with the present invention may be synthesized in accordance with conventional linkage reactions which are well known among those skilled in the art. An example, in which the polymeric backbone $R^1$ is functionalized with multiple amine groups, such as polylysine, is offered below. In this example, the backbone is referred to as (AMP)(—NH$_2$)$_x$, "AMP" denoting the amplifying effect of permitting the attachment of a multitude of spacers and paramagnetic complexes, and x representing a number corresponding to n is Formula I.

The attachment of a polyethylene glycol (PEG) spacer to the amplifier may be achieved by using an activated ester of PEG, such as an α,ωbis-p-nitrophenoxy ester of PEG:

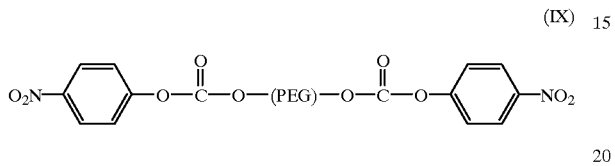
(IX)

in which "PEG" is polyethylene glycol minus the terminal hydroxyl groups, as defined above. An excess of this derivatized PEG ester IX is reacted with (AMP)(—NR$_2$)$_x$ to yield the intermediate:

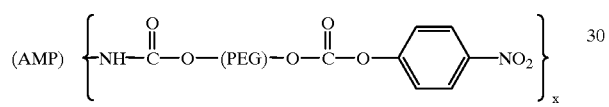
(X)

The intermediate is then reacted with an excess of H$_2$N—(Ligand), which denotes the ligand of the paramagnetic complex derivatized to contain a functional amine group. The product is the construct:

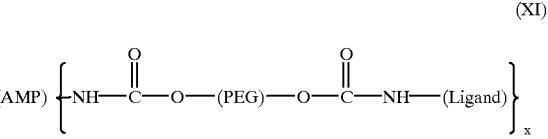
(XI)

In an alternative scheme to a similar product, the above intermediate X is converted to a second intermediate with a terminal amine group, by reaction with a diamine such as NH$_2$—(CH$_2$)$_2$—NH$_2$. The second intermediate has the structure:

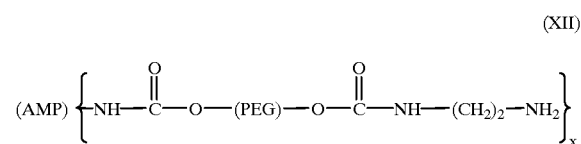
(XII)

This intermediate XII is then reacted with a carboxyl-activated ligand, such as, for example, an anhydride of the ligand, to produce a construct having the formula:

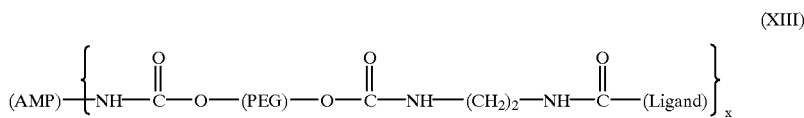
(XIII)

A cleavable group such as disulfide can be introduced by reacting the intermediate X with a diamine containing an internal disulfide, such as cysteamine disulfide, NH$_2$—CH$_2$)$_2$—S—S—(CH$_2$)$_2$—NH$_2$, to yield the further intermediate:

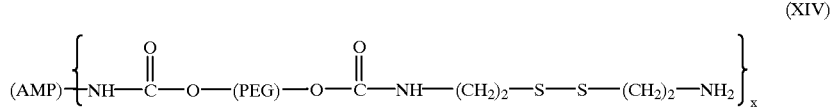
(XIV)

This may then be reacted with a carboxyl-activated ligand, to yield:

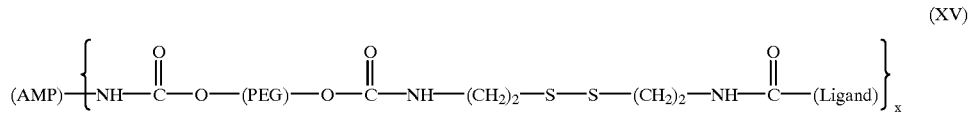
(XV)

Many further alternatives to these schemes exist. To produce constructs containing cleavable esters in the spacers without PEG, for example, an amine- or hydroxyl-containing amplifying polymer can be derivatized to produce carboxylic acid groups as the functional groups. This is readily achieved by reacting the polymer with maleic, succinic or glutaric anhydride using established procedures. A derivatized ligand to combine with the derivatized polymer can be formed by reacting a ligand bearing an isothiocyanate group with an amino alcohol, $HO(CH_2)NH_2$, to place a terminal hydroxyl group on the ligand. The carboxylic acid group on the derivatized polymer can then be activated by conventional methods using such agents as dicyclohexyl-carbodiimide or carbonyl-diimidazole, and reacted with the derivatized ligand to achieve the ester linkage. The section of the construct between the amplifying polymer and the ligand serves as the spacer, and the length of the spacer is determined by the number of $CH_2$ groups in the amino alcohol used to derivative the ligand.

In an alternate scheme which produces a reverse ester, the ligand is derivatized with an aminocarboxylic acid, $HO_2C(CH_2)_2NH_2$, rather than an amino alcohol. The resulting carboxylic acid-derivatized ligand is then activated with dicyclohexylcarbodiimide or carbonyldiimidazole and coupled directly to a hydroxyl-containing amplifying polymer.

In either of these two schemes, a selected fraction of the amine or hydroxyl groups which are native to the amplifying polymer can be protected if desired, to avoid interference with the coupling reactions. This is readily achieved by conventional methods, notably acetylation with acetic anhydride.

Ligands with functional groups for attachment to the spacer can be prepared by conventional methods. Well-known ligands for example are readily derivatized by methods known to those skilled in the art. It is preferable to select a ligand which retains all or most of its strength and stability in holding the metal ion even after derivatization.

In another embodiment, the present invention provides pharmaceutical compounds of formula XVI:

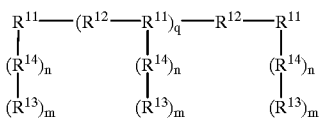

The symbol $R^{11}$ in this formula represents a multifunctional group providing a multitude of attachment sites for spacer groups. Polymers, including polypeptides, polysaccharides and others, are generally useful for this group. With its multitude of attachment sites, $R^{11}$ serves as an amplifying function for the paramagnetic complexes. Each multifunctional group may be the same or different and will be connected to at least one other multifunctional group by means of a biodegradeable linking group $R^{12}$. The biodegradeable linking groups may also be the same or different. The portion of the compound comprising $R^{11}$—$(R^{12}$—$R^{11})_q$—$R^{12}$—$R^{11}$ makes up the backbone of the MMCM construct with q being an integer of from zero to five.

The symbols $R^{14}$ and $R^{13}$ represent a spacer group and a paramagnetic complex, respectively, or the spacer group and a ligand which retains the paramagnetic metal cation and thus forms part of the paramagnetic complex. The symbol m represents the number of paramagnetic complexes attached to each spacer. This may be as low as 1, or greater. The symbol n represents the number of spacers, and their associated complexes, which are attached to the associated multifunctional group, and this will generally be a number in excess of 1, preferably well in excess of 1. The term "ligand" will be used herein for $R^{13}$ for purposes of convenience, but will refer to both the ligands which combine with the paramagnetic metal cations to form the paramagnetic complexes, and to the complexes themselves.

The groups $R^{11}$ are generally those which are described for $R^1$ of formula I. Preferred groups for $R^{11}$ are those having lower molecular weights than the corresponding backbone of formula I such that when the $R^{11}$ groups are taken together with the biodegradeable linking groups, $R^{12}$, the overall molecular weight of the backbone is from about 40,000 to 100,000. For example, in one embodiment of formula XVI, the backbone would include a tetramer of dextrans, each having a molecular weight of about 15,000–20,000 and being connected in a linear array by linking groups which are cleavable in vivo. The linking groups $R^{12}$ are the same as those which are described for $R^2$ of formula I and will contain any of a variety of groups as part of its chain which will cleave in the blood stream at a rate which is enhanced relative to that of constructs which lack such groups. Accelerated rates of cleavage enhance the rates of removal of the potentially toxic paramagnetic ions from the body, and therefore lower the toxicity. Accelerated cleavage rates further permit the administration of higher concentrations of the paramagnetic ions, thereby increasing the MR image contrast. While the degree of cleavage rate enhancement is not critical to the invention, preferred examples of these spacers are those in which at least about 10% of the cleavable groups are cleaved in the blood stream within 24 hours of administration, most preferably at least about 35%. Preferred cleavable groups are ester linkages and disulfide linkages.

The ligands represented by $R^{13}$ are typically the same as those described above for $R^3$ of formula I and include any ligand useful as an MR imaging contrast enhancement agent which can be attached to a spacer. These include known ligands which have been modified or derivatized in any of a variety of ways to achieve a functional group which will permit attachment to the spacer.

The spacer $R^{14}$ can be any of a wide variety of molecular structures, and will be at least bifunctional to permit attachment to both $R^{11}$ and $R^{13}$, optionally through linkage groups. Spacers with multiple binding functionalities at the complex end (i.e., the $R^{13}$ end) will accommodate a multitude of complexes, in which case m will have a value exceeding 1. Spacers of this type serve an amplifying function in a manner similar to that of the $R^{11}$ group in the backbone, although to a lesser extent. Other spacers useful in the invention will have only a single functionality at either end, in which case the value of m will be 1. Useful spacers will be those which are non-toxic and non-immunogenic, while those which are particularly useful will be those which have further properties which benefit the construct when administered as MMCM. These properties include in vivo cleavability and hydrophilicity. Still other useful properties are the ability to lower antigenicity and to increase molecular weight. Spacers with still further properties can be utilized to advantage as well, as will be readily apparent to those skilled in the art.

The spacer $R^{14}$ may be either a straight-chain or a branched-chain structure. Preferred $R^{14}$ groups are those which include a straight chain within their structures, either as the entire spacer group or as the backbone of a branched-chain group. The straight chain may be a chain of carbon atoms or of carbon atoms interrupted with one or more hetero atoms such as oxygen atoms, sulfur atoms or nitrogen atoms. The bonds forming the chain may be single bonds or double bonds, although single bonds are preferred. The length of the chain is not critical and may vary widely, depending on the desired relationship between the molecular weight of the construct and the number of paramagnetic groups included on the construct. Best results will generally be obtained with chain lengths ranging from 4 atoms to 1,000 atoms, with preferred chains being those of 6 atoms to 100 atoms, and the most preferred being those of from 10 atoms to 50 atoms. The chain as thus described is the backbone of the spacer itself, and does not include atoms, groups or side chains bonded to the serially bonded atoms forming the backbone. It does however include linking groups at the chain termini joining the chain to $R^{11}$ and $R^{13}$, when such linking groups are present.

The present invention also contemplates embodiments of formula XVI in which the backbone is a cyclic array of $R^{11}$ and $R^{12}$ rather than the linear array depicted in formula XVI. These cyclic embodiments will be identical to those of formula XVI with the addition of one linking group, $R^{12}$, which connects the two terminal $R^{11}$ groups.

Finally, the present invention contemplates related embodiments in which multiple $R^{11}$—($R^{14}$—$R^{13})_m)_n$ moieties are covalently attached to a central template. In one embodiment, the central template is an aromatic template or a polycyclic aromatic template. Examples of preferred aromatic templates are benzene rings, naphthalene, anthracene and phenanthrene rings.

Synthesis of the compounds of formula XVI are by techniques which are well known to those of skill in the art. Strategies will follow those discussed for the compounds of formula I with only slight modifications. For example, the synthesis of a compound of formula XVI in which each $R^{11}$ is a dextran of molecular weight 20,000 and q is 2, can proceed in a concerted fashion by first joining two dextrans to each other. This is most efficiently accomplished by attaching each of two dextrans to a biodegradeable linker (i.e. cystamine) using reductive amination. The resulting two pairs of linked dextrans can then be attached via a third linking group to provide the backbone for the MMCM construct. Having synthesized the backbone, the metal complexes can then be attached by methods described below for compounds of formula I.

The following examples are offered for purposes of illustration, and are intended neither to limit nor to define the invention in any manner.

EXAMPLES

Materials

Dextran (MW 40,000, 70,000) was purchased from Sigma Chemical Company, and was dried under vacuum (0.1 mm Hg) over $P_2O_5$ at 100° C. for 24h prior to use. Formamide and pyridine were ACS grade and were used as purchased from Fischer Scientific (Fair Lawn, N.J., USA). Cystamine dihydrochloride, p-nitrophenylchloro-formate, chlorotriphenylmethane, 6-aminocaproic acid, dicyclohexylcarbodiimide (DCC), and N,N-dimethylaminopyridine (DMAP), were used as purchased from Aldrich Chemical Company (Milwaukee, Wis., USA). The gadolinium complexes of 10-(3-(4-isothiocyanatophenoxy)-2-hydroxypropyl)-1,4,7-tris(carboxymethyl)-1,4,7,10-tetraazacyclododecane and 10-(2-hydroxy-3-(4-carboxyphenoxy)-propyl)-1,4,7-tris(carboxymethyl)-1,4,7,10-tetraazacyclododecane were generously provided by Schering AG and can be prepared by the methods disclosed in U.S. Pat. No. 5,277,895 incorporated herein by reference.

Methods

NMR spectroscopy was performed on a GE QE-300 instrument. The spectra were referenced to the residual proton peaks of the sample solvent. Elemental analyses (C, H, N, Gd) were performed by Schwarzkopf Analytical Laboratory (Woodside, N.Y., USA).

In vitro plasma digestion studies were performed as follows. Typically, a solution of the macromolecular contrast agent (MMCM, ≈50 mg/mL) was prepared in buffer (0.1 M sodium phosphate, pH 7.4). This concentration was sufficient to give a digestion mixture which, when diluted 10-fold had an optical density of 1.0–2.0 at the $\lambda_{max}$. The experiment was started when a 200 μL aliquot of the solution was added to 800 μL of human plasma, vortexed and incubated at 37° C. The macromolecular component of the MMCM was separated from the cleaved small molecular chelate using Centrex centifugal ultrafilters (MWCO 3000). Aliquots of the digestion mixture were withdrawn, placed into the upper receptacle of the Centrex units and centrifuged. The small molecular components passed through the membrane into the collection receptacle. The collected solution was diluted to a known volume and the UV spectrum was measured. Specifically, the optical density at either 240 or 284 nm was measured. A plasma "blank" was prepared by diluting a sample of human plasma with 200 μL of buffer and incubating at 37° C. After ultrafiltration the spectrum of the small molecular component of the plasma "blank" was measured and subtracted from the spectrum of the MMCM digestion sample. This allowed compensation for any spectral contribution from small molecular components of the plasma which were not retained by the ultrafilter. The digestion studies were run until the gadolinium chelates of the MMCM were, at least, 90% cleaved and available for ultrafiltration.

Example 1

This example illustrates the synthesis of a gadolinium chelate as an example of a paramagnetic complex which can be attached to a suitable backbone with a spacer group.

One example of a ligand which can be derivatized to contain a coupling functionality and still retain strong chelating characteristics is 1,4,7,10tetraaza-cyclododecanetetraacetic acid (DOTA). This ligand can be derivatized by substituting a functional group for one of the four carboxylic acid groups. A synthesis scheme for preparing this type of derivatized DOTA is as follows.

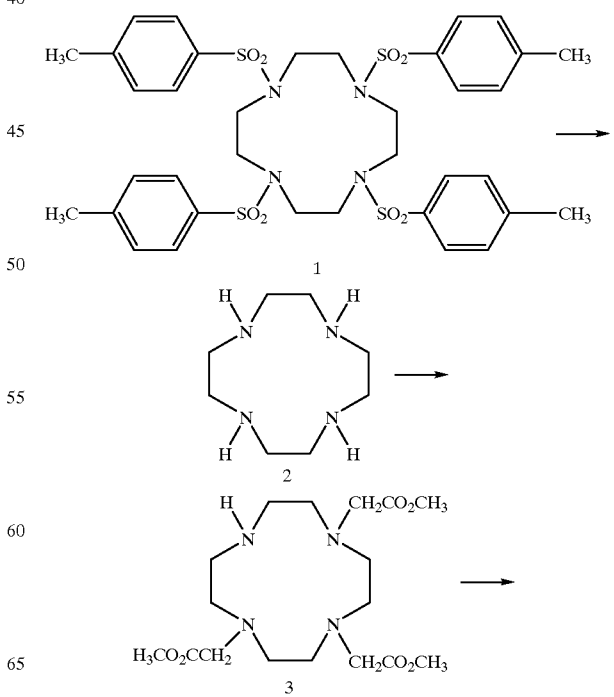

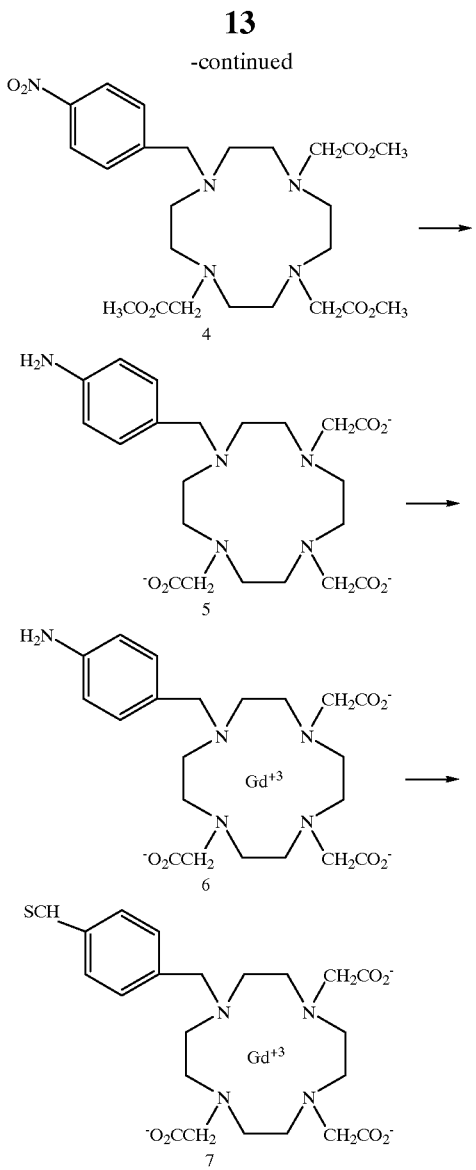

This synthesis was performed as follows.

The tetraazamacrocycle (1) was prepared by the method of Atkins, as reported by Atkins, T. J., Richman, J. E., and Oettle, W. F., in *Organic Synthesis Collective Volume IV*, John Wiley & Sons: New York, 1988, pages 652–662. The trimethyl ester (3) was prepared by the method of Kline, as reported by Kline, S. J, Betebenner, D. A., and Johnson, D. K., *Bioconjugate Chem.* 2, pages 26–31 (1991).

A reaction flask was then charged with the trimethyl ester (3) (413.0 mg, 1.1 mmol), 4-nitrobenzyl bromide (230.2 mg, 1.1 mmol) and $Na_2CO_3$ (255 mg, 2.1 mmol) in 10 mL acetonitrile, and the contents were stirred for 16 hours at 45° C. under nitrogen. The mixture was then cooled to 25° C. and filtered through Celite. The filtrate was evaporated to dryness and the residue was taken up in methylene chloride (15 mL), washed with water (1×5 mL), dried over sodium sulfate and evaporated to dryness. Column chromatography of the crude product on silica, using $CH_2Cl_2$ (20 mL) followed by $CH_2Cl_2/CH_3OH$ (20:1, 30 mL), with isolation of the more polar fraction gave N-(4-nitrobenzyl)-1,4,7,10-tetraazacyclododecane-N',N'',N'''-triacetic acid trimethyl ester (4) as a pale yellow oil (384.2 mg, 60% yield).

The nitrobenzyl-substituted macrocycle (4) (310.8 mg, 0.59 mmol) in methanol (3 mL) was treated with a suspension of $PtO_2$ (35 mg) in methanol (5 mL) which had been hydrogenated for 5 minutes at 25 psi. A balloon containing $H_2$ was fixed to the top of the flask and the suspension was stirred for 16 hours at 25° C. The suspension was filtered through Celite and the filtrate was transferred to a round-bottomed flask. A solution of LiOH (1.03 M, 1.72 mL, 1.77 mmol) was added with stirring. The mixture was stirred for 26 hours, then evaporated to dryness yielding lithium N-(4-aminobenzyl)-1,4,7,10-tetraazacyclododecane-N',N'',N'''-triacetate (5) as a white powder (274.3 mg, 99%).

A solution of this compound (5) (250.0 mg, 0.53 mmol) in water (6 mL) was treated with a solution of $GdCl_3$ (17.1 mL, 0.53 mmol) and stirred for 16 hours at 60° C. The solution was evaporated to dryness and the residue was dissolved in methanol (3 mL). A white solid was then precipitated by the addition of acetone (50 mL). The resulting suspension was stirred for 3 hours, then filtered. The filter cake was washed with acetone (2×10 mL) and diethyl ether (1×10 mL). The solid was dried under vacuum for 24 hours, affording Gd(III)-N-(4-aminobenzyl)-1,4,7,10-tetraazacyclododecane-N',N'',N'''-triacetate (6) as a white solid (303 mg, 94% yield).

The 4-aminobenzyl compound (6) was then converted to the 4-thiocyanato compound (7) by treatment with thiophosgene. The structure of the product was confirmed by nuclear magnetic resonance spectrometry and infrared spectrophotometry.

Example 2

This example illustrates the synthesis of a Dextran-based MMCM with a cleavable disulfide linkage.

A. Reaction of dextran with p-nitrophenylchloroformate to produce the activated dextran 8.

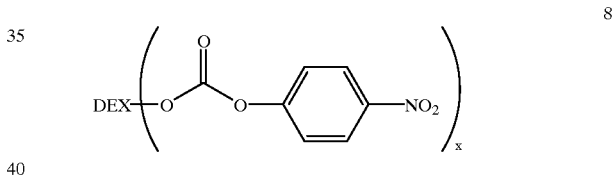

Dextran (MW 70,000, 1.00 g, 10.92 mmol anhydroglucose units) in DMSO/pyridine (1:1, 100 mL) was treated at 4° C. with 4-nitrophenylchloroformate (1.77 g, 8.78 mmol). After ~10 min a white solid began to separate. The mixture was maintained at 4° C. and stirred for 4 hours. The polysaccharide was precipitated by pouring the reaction mixture into ethanol/ether (1:1, 400 mL). The suspension was stirred for 30 min then allowed to settle. The solvent was removed by decantation and the solid derivative was isolated by filtration, washed with ethanol (3×20 mL) and ether (3×20 mL). The resulting white solid was dried under vacuum (0.05 mm Hg, 25° C.) for 24 hours to yield 1.346 g of 8 (degree of substitution (DS), 2.08 mmol, 1 4-nitrophenyl carbonate unit/5.2 anhydroglucose units).

B. Monofunctionalization of cystamine with chlorotriphenylmethane to produce protected linker arm 9.

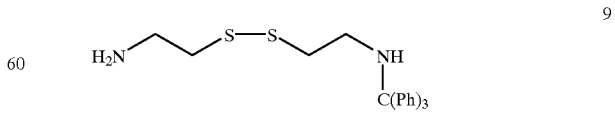

Cystamine dihydrochloride (6.971 g, 27.31 mmol) was dissolved in $H_2O$ (30 mL) and dioxane (30 mL) was added. Triethylamine (8.30 g, 81.9 mmol) was added with stirring. A solution of chlorotriphenylmethane (2.54 g, 9.10 mmol) in dioxane (20 mL) was added dropwise over 45 min. The mixture was stirred for 48 hours. The dioxane was removed by rotary evaporation and the aqueous mixture was diluted with H$_2$O (20 mL) and extracted with HCCl$_3$ (3×25 mL). The extracts were pooled, washed with H$_2$O (1×15 mL), sat'd NaHCO$_3$ (1×15 mL) and H$_2$O (1×15 mL). The organic layer was dried (Na$_2$SO$_4$), filtered and evaporated to dryness. The residue was purified by flash chromatography on silica (HCCl$_3$ then HCCl$_3$/MeOH, 9:1). After evaporation of the appropriate fractions a pale yellow oil 2.58 g, (72% based on chlorotriphenylmethane) was isolated. NMR (DCCl$_3$) δ 2.479 (t, J=6.3 Hz; 2H), 2.560 (t,J=6.0 Hz; 2H); 2.825–2.921 (m, 4H); 7.164–7.495 (m, 15H). Anal. C$_{23}$H$_{26}$N$_2$S$_2$ (0.3 MeOH). Calc'd. C 69.24; H 6.78; N 6.93. Found C 69.37; H 6.77; N 6.58. TLC (MeOH:NH$_4$OH:HCCl$_3$, 1:0.2:9), R$_f$=0.6.

C. Coupling of protected linker arm 9 to activated dextran 8 to produce 10.

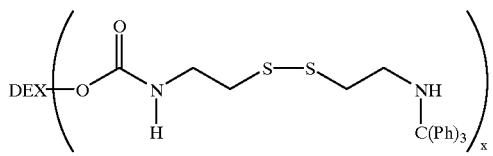

10

A solution of activated dextran (673.8 mg, 0.41 mmol activated hydroxyl units) in formamide/pyridine (1:1, 40 mL) was treated with a solution of monoprotected cystamine 9 (508 mg, 1.3 mmol) and triethylamine (142 mg, 1.2 mmol) in formamide/pyridine (1:1, 20 mL). The amine solution was added dropwise over 10 min during which time the colorless polysaccharide solution turned bright yellow. The resulting solution was stirred for 16 h. The polysaccharide was precipitated by adding the solution to ethanol/ether (3:1, 400 mL). The suspension was stirred for 30 min then allowed to settle. The solvent was decanted off and the solid was isolated by filtration. The filter cake was dried at 50° C. under vacuum (0.5 mm Hg) for 16 h giving 540.3 mg (65% recovery based on theoretical yield) of a pale tan solid. NMR (d6-DMSO) δ 2.487–3.614 (m); 4.493–4.856 (m); 7.283–7.958 (m).

D. Deprotection of the carrier amine group to produce 11.

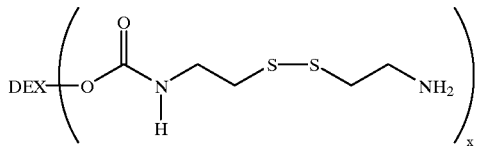

11

The amine-protected carrier 10 (314.4 mg) was suspended in trifluoroacetic acid/H$_2$O (1:24, 25 mL) and ether (40 mL). The suspension was stirred for 16 hours. The organic and aqueous layers were separated and the aqueous layer was extracted with ether (2×10 mL). The aqueous layer was lyophilized giving 120 mg of a cream colored powder which gave a positive ninhydrin reaction. NMR(D$_2$O) δ 3.73 (m); 4.985 (s). Anal. Calc'd for D.S. 0.17, (C$_6$H$_{12}$O$_6$) (C$_7$H$_{12}$N$_2$O$_3$S$_2$F$_3$)$_{0.17}$. Calc'd. C 40.41; H 6.62; N 2.19. Found C 40.26; H 6.92; N 1.85.

E. Determination of free sulfhydryl groups in the macromolecular carrier (Ellmann's reagent)

To ensure that the essential disulfide link had not been reduced or otherwise degraded to free sulfhydryl during deprotection, an assay for sufhydryl groups was performed with Ellmann's reagent. A solution of deprotected carrier 11 (2.6 mg) in 0.1 M sodium phosphate buffer, pH 8 (2.0 mL) was treated with a standard solution (20 μL of Ellmann's reagent (39.6 mg) in 0.1 M sodium phosphate, pH 7 (5 mL). The absence of an absorbance at 412 nm in the UV spectrum of the resulting solution confirmed the absence of free sulfhydryl groups.

F. Conjugation of the disulfide amino carrier 11 with a benzylisothiocyanate derivatized Gd macrocycle to produce the dextran-based MMCM, 12.

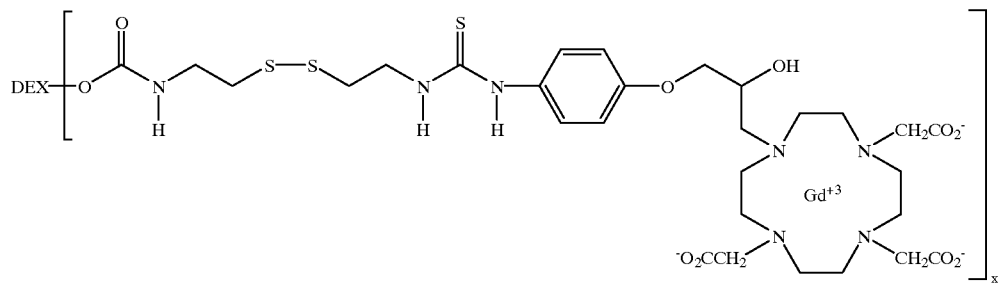

12

A solution of carrier 11 (109 mg) in 0.1 M HEPES, pH 8.8 (5 mL) was treated with a solution of Gd chelate 1 (100 mg, 0.141 mmol) in formamide (2 mL). The resulting mixture was stirred for 16 h then transferred to a dialysis bag (MWCO 12,000). The solution was dialyzed against distilled water (4×4 L) for a total of 16 h then lyophilized giving 120 mg of a pale tan solid. Analytical gel permeation chromatography (GPC) on a column of Sephadex G-25 (2×20 cm) produced a chromatogram with only one peak which eluted at the column void volume. This material was negative to ninhydrin. Anal. Gd(III) 2.78%; corresponding to 16 mol Gd(III)/mol dextran.

Example 3

This example illustrates the syntheses of two Dextran-based MMCMs, each having a cleavable ester linkage.

A. Direct esterification of dextran with a benzoic acid derivatized Gd chelate to produce MMCM. 13.

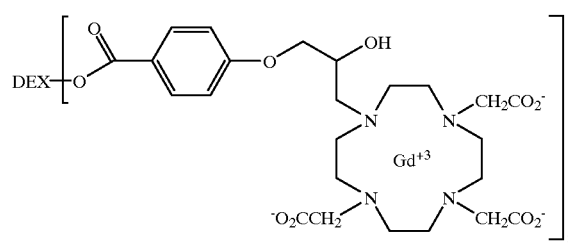

13

A solution of the gadolinium complex of 10-(2-hydroxy-3-(4-carboxyphenoxy)-propyl)- 1,4,7-tris(carboxymethyl)-1,4,7,1 0-tetraazacyclododecane (500 mg, 0.72 mmol) in pyridine/formamide (1:1, 10 mL) was cooled to 0° C. with stirring. Dicyclohexylcarbodiimide (DCC, 149 mg, 0.72 mmol) and N,N-dimethylaminopyridine (DMAP, 20 mg, 0.16 mmol) were added. The resulting solution was stirred for 30 min at 0° C. A solution of dextran (MW 40,000; 1.0 g, 0.025 mmol) in formamide/pyridine (1:1, 30 mL) was prepared by gently warrning a suspension of the polysaccharide. The dextran solution was added to the activated chelate and the mixture was stirred at 25° C. for 4 days. During this time a precipitate of dicyclohexylurea formed. The suspension was filtered and the polysaccharide was precipitated by dropwise addition of the filtrate into ethanol/ether (1:2, 300 mL). The suspension was stirred for 30 min then allowed to settle. The solvent was decanted off and the solid was isolated by filtration. The product was purified by GPC on a column of Sephadex G-25 eluted with distilled $H_2O$. Fractions corresponding to the macromolecular component were collected, pooled and lyophilized. To ensure there were no small molecular components unremoved by GPC an analytical sample was prepared by ultrafiltration (Centrex MWCO 10,000) of an aqueous solution (500 μL) containing the product (300 mg). The retentate was collected and lyophilized giving a white pad (296 mg). The UV spectrum of an aqueous solution of this product (0.175 mg/mL) had an absorbance at 258 nm which confirmed the presence of the benzoic acid ester. The analytical sample contained 0.92% gadolinium, corresponding to approximately 3 mol Gd/mol dextran.

A. Esterification of dextran with a 6-aminocaproic acid linked Gd chelate to produce MMCM, 14.

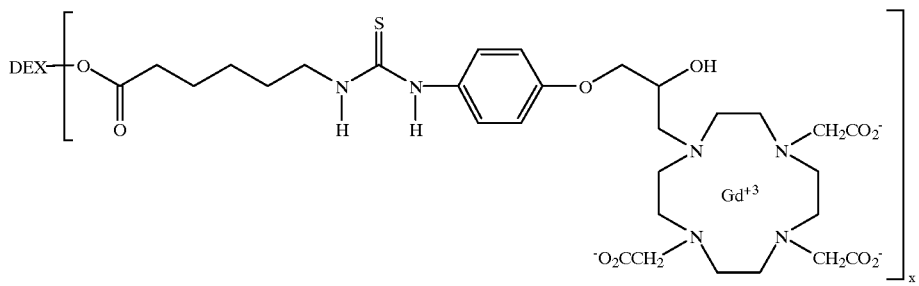

14

A solution of the gadolinium complex of 10-(3-(4-isothiocyanatophenoxy)-2-hydroxypropyl)-1,4,7-tris (carboxymethyl)-1,4,7,10-tetraazacyclododecane (303.5 mg, 0.43 mmol) in formamide/pyridine (1:1, 6 mL) was treated with 6-aminocaproic acid (56 mg, 0.43 mmol) and $H_2O$ (0.5 mL) was added. The solution was stirred for 3 days then the pyridine and $H_2O$ were removed by rotary evaporation. The derivatized chelate was precipitated by dropwise addition of the formamide solution to ethanol (40 mL). The solid was washed with ethanol (1×10 mL), ether (1×10 mL) and dried under vacuum (0.5 mm Hg, 25° C.) giving a pale tan solid (253.8 mg, 70%). This product was redissolved in formamide/pyridine (1:1, 6 mL) and cooled to 0° C. as DCC (62 mg, 0.30 mmol) and DMAP (20 mg, 0.1 6 mmol) were added. The mixture was stirred for 30 min then a solution of dextran 70,000 (300 mg) in formamide/pyridine (1:1, 10 mL) was added. The resulting solution was stirred for 4 days, during which time dicyclohexylurea precipitated. The suspension was filtered and the polysaccharide was precipitated by dropwise addition of the filtrate to ethanol/ether (1:1, 300 mL). The suspension was stirred for 30 min then allowed to settle. The solvent was decanted off and the solid was isolated by filtration and dried under vacuum (0.5 mm Hg, 25° C.), giving 412 mg of a pale tan solid which was purified by GPC. The appropriate fractions were pooled and lyophilized giving 318 mg of a pale tan powder. An analytical sample was prepared by ultrafiltration (Centrex, MWCO 3000) of the product in $H_2O$ (1.0 mL) and lyophilization of the retentate which gave 305 mg of a pale tan powder. The analytical sample contained 2.27% gadolinium, corresponding to approximately 11 mol Gd/mol dextran.

EXAMPLE 4

This example illustrates the results of plasma digestion with the Dextran-based Gd chelates.

A. Plasma digestion of disulfide linked MMCM, 12.

The plasma degradation of the disulfide linked MMCM 12 was investigated (see general considerations). A stock solution of 12 (52 mg) in 0.1 M sodium phosphate buffer, pH 7.4 (1.0 mL) was prepared. An aliquot (200 μL) of the stock solution was added to plasma (800 μL). The solution of 12 was incubated in plasma, at 37° C., for 24 h, ultrafiltered, and the UV absorbance at 282 nm of an aliquot of the filtrate was recorded. The extent of disulfide cleavage estimated from the absorbance at 282 nm was 92%. A blank was prepared by diluting the stock solution (200 μL) with buffer. The blank was incubated and ultrafiltered parallel to the plasma digest sample. The extent of cleavage in the blank was 11%.

B. Plasma digestion of ester linked MMCM, 13.

The plasma degradation of the ester linked MMCM 13 was investigated (see general considerations). A stock solution of 13 (52 mg) was prepared in 0.1 M sodium phosphate buffer, pH 7.4 (1.0 mL). An aliquot (200 μL) of the solution of 13 was incubated in plasma for 48 h, ultrafiltered, and the UV absorbance at 258 nm of an aliquot of the filtrate was recorded. The extent of ester cleavage estimated from the absorbance at 258 nm was 27%. At 96 h the extent of cleavage was approximately 100%. A blank was prepared by diluting the stock solution (200 μL) with buffer. The blank was incubated and ultrafiltered parallel to the plasma digest sample. At 48 h the extent of cleavage in the blank was 19%. At 96 h the blank was 34% cleaved.

C. Plasma digestion of 6-aminocaproic ester linked MMCM, 14.

The plasma degradation of the 6-aminocaproic acid linked MMCM 14 was investigated (see general considerations). A stock solution of 14 (47 mg) in 0.1 M sodium phosphate buffer, pH 7.4 (1.0 mL) was prepared. An aliquot of the stock solution (200 μL) was dissolved in plasma (800 μL). A blank was prepared by diluting the stock solution (200 μL) with buffer. The plasma samples containing 14 were incubated for 48 h, ultrafiltered, and the UV absorbance at 240 nm of an aliquot of the filtrate was recorded. At 48 h the extent of cleavage of 14 in plasma was 100%. At 48 h the blank was also 100% cleaved.

Administration of the constructs of the present invention for purposes of MR imaging is achieved by conventional procedures. Aqueous solutions of the constructs are most conveniently used. The concentrations of the constructs in these solutions and the amounts administered may vary widely, the optimum in each case varying with the strength of the magnetic moment of the paramagnetic metal in the agent, the contrast enhancement strength of the paramagnetic complex as a whole, the method of administration, the degree of contrast enhancement desired or needed, and the age, weight and condition of the patient or subject to whom administration is made. In most cases, best results are obtained with solutions at concentrations of about 0.05 to about 2.0 equivalents of the paramagnetic complex per liter, preferably about 0.1 to about 1.0 mole per liter. Likewise, best results in most cases are usually obtained with dosages ranging from about 0.01 to about 1.0 millimole of agent per kilogram of whole body weight (mM/kg), preferably from about 0.05 to about 0.5 mM/kg. Administration may be achieved by any parenteral route and method, most notably by intravenous administration. The rate of administration may likewise vary, best results generally being obtained at rates ranging from about 0.1 mM/min/kg to about 1.0 mM/min/kg.

The foregoing is offered primarily for purposes of illustration. It will be readily apparent to those skilled in the art that additional substitutions, modifications and other variations of the constructs, their methods of preparation and their methods of use may be practiced without departing from the spirit and scope of the invention.

What is claimed is:

1. A pharmaceutical agent having the formula:

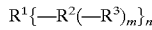

in which:
  $R^1$ is a polysaccharide group which is non-toxic and non-antigenic;
  $R^2$ is a group which includes at least four atoms bonded together and adjoining $R^1$ to $R^3$ and is a member selected from the group consisting of
  $X-R^4-Y-R^5-Z$, $X-R^5-Y-R^4-Z$ and $X-(CH_2)_t-R^5-(CH_2)_u Z$ in which:
  $R^4$ is polyethylene glycol having a formula weight of from about 100 to about 20,000 daltons;
  $R^5$ is a member selected from the group consisting of $C(O)-O$ and $O-C(O)$, such that at least 10% of all $R^5$ groups are degraded in plasma after 24 hours;
  X, Y and Z are inert linking groups and are members selected from the group consisting of $(CH_2)_q-NH$, $NH-(CH_2)_q$, $NH-C(O)-O$, $O-C(O)-NH$, $(CH_2)_q-NH-C(O)-O$, $O-C(O)-NH-(CH_2)_q$, $NH-C(S)$, and $C(S)NH$;
  $R^3$ is a complex of a ligand and a paramagnetic metal cation capable of altering contrast in magnetic resonance imaging;
  m is at least 1;
  n is at least 3;
  q is a number from 1 to 10; and
  t+u is at least 2.

2. The pharmaceutical agent according to claim 1 in which $R^2$ includes a chain of from 4 atoms to 1,000 atoms serially bonded together.

3. The pharmaceutical agent according to claim 1 in which $R^2$ includes a chain of from 6 atoms to 100 atoms serially bonded together.

4. The pharmaceutical agent according to claim 1 in which $R^2$ includes a chain of from 10 atoms to 50 atoms serially bonded together.

5. The pharmaceutical agent according to claim 1 in which said polyethylene glycol portion has a formula weight ranging from about 200 to about 1,000 daltons.

6. The pharmaceutical agent according to claim 1 in which q is 2 to 4.

7. The pharmaceutical agent according to claim 1 in which q is 2.

8. The pharmaceutical agent according to claim 1 in which $R^2$ is:

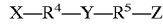

in which:
  X is $NH-C(O)-O$;
  Y is $O-C(O)-NH-(CH_2)_q$; and
  Z is $(CH_2)_q-NH$.

9. The pharmaceutical agent according to claim 1 in which $R^2$ is:

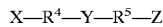

in which:
  X is $NH-C(O)-O$;
  Y is $O-C(O)-NH-(CH_2)_q$, in which q is 1 to 10; and
  Z is $(CH_2)_q-NH$, in which q is 1 to 10.

10. The pharmaceutical agent according to claim 1 in which $R^2$ is:

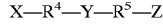

in which:
  X is $NH-C(O)-O$;
  Y is $O-C(O)-NH-(CH_2)_2$; and
  Z is $(CH_2)_2-NH$.

11. A pharmaceutical agent having the formula

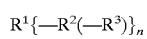

in which:
  $R^1$ is a polysaccharide group which is non-toxic and non-antigenic;
  $R^2$ is a group having the formula

  X'—$R^6$—Z' in which:
  X' and Z' are the same or different and are inert linking groups selected from the group consisting of $(CH_2)_q$—NH, NH—$(CH_2)_q$, NH—C(O)—O, O—C(O)—NH, $(CH_2)_q$—NH—C(O)—O, O—C(O)—NH—$(CH_2)_q$, NH—C(S), and C(S)NH; and
  $R^6$ has the formula

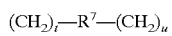
  $(CH_2)_t$—$R^7$—$(CH_2)_u$ in which:
  $R^7$ is a member selected from the group consisting of C(O)—O, and O—C(O), such that at least 10% of all $R^7$ groups being degraded in plasma after 24 hours;
  t is zero or a positive integer, and u is zero or a positive integer, such that the sum of t+u is at least 2;
  $R^3$ is a complex of a ligand and a paramagnetic metal cation capable of altering contrast in magnetic resonance imaging; and
  n is at least 3.

12. The pharmaceutical agent according to claim 11, in which:
  t is 2 to 10; and
  u is 2 to 10.

13. The pharmaceutical agent according to claim 11, in which:
  t is 2 to 6; and
  u is 2 to 6.

14. A pharmaceutical agent having the formula

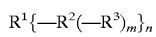
  $R^1\{-R^2(-R^3)_m\}_n$ in which:
  $R^1$ is a polysaccharide which is non-toxic and non-antigenic;
  m is at least 2;
  $R^2$ has the formula

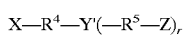
  X—$R^4$—Y'(—$R^5$—Z)$_r$ in which:
  $R^4$ is polyethylene glycol having a formula weight of from about 100 to about 20,000 daltons;
  $R^5$ is a member selected from the group consisting of, C(O)—O, and O—C(O), such that at least 10% of all $R^7$ groups are degraded in plasma after 24 hours;
  X is NH—C(O)—O;
  Y' is O—C(O)—NH—$(CH_2)_q$—$CH_3$ in which q is 1 to 3, and a number equal to m of the H atoms bonded to the C atoms are substituted by NH—$(CH_2)_s$—NH where s is 2 to 4;
  Z is $(CH_2)_q$—NH in which q is 2 to 4; and
  r is zero or m; and
  $R^3$ is a complex of a ligand and a paramagnetic metal cation capable of altering contrast in magnetic resonance imaging; and
  n is at least 3.

15. A pharmaceutical agent in accordance with claim 14 in which r is m.

16. A pharmaceutical agent in accordance with claim 14 in which m is 2 to 6 and r is m.

17. A pharmaceutical agent in accordance with claim 14 in which m is 2 or 3 and r is m.

18. A pharmaceutical agent in accordance with claim 14 in which the product m×n is at least 10.

19. A pharmaceutical agent in accordance with claim 14 in which the product m×n is 10 to 1,000.

20. A pharmaceutical agent in accordance with claim 14 in which the product m×n is 30 to 300.

21. A pharmaceutical agent in accordance with claim 14 in which the $R^1$ is a member selected from the group consisting of dextran, and poly(aminopropyl)dextran.

22. A pharmaceutical agent in accordance with claim 14 in which $R^3$ is a chelate comprised of a paramagnetic metal cation and a chelating agent.

23. A pharmaceutical agent in accordance with claim 22 in which said chelating agent is a macrocyclic chelating agent.

24. A pharmaceutical agent in accordance with claim 22 in which said paramagnetic metal cation is gadolinium (III) and said chelating agent is a macrocyclic chelating agent.

25. A pharmaceutical agent in accordance with claim 22 in which said paramagnetic metal cation is gadolinium (III) and said chelating agent is 1,4,7,10-tetraaza-cyclododecane-N,N',N'',N'''-tetraacetic acid.

26. A pharmaceutical agent in accordance with claim 22 in which said paramagnetic metal cation is gadolinium (III) and said chelating agent is 1,4,7,10-tetraaza-cyclododecane-N,N',N''-triacetic acid.

27. A pharmaceutical agent having the formula:

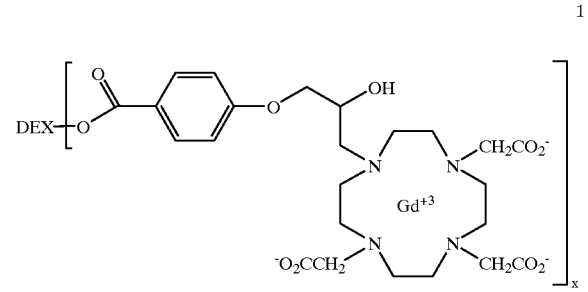

wherein x is at least 3.

28. A pharmaceutical agent having the formula:

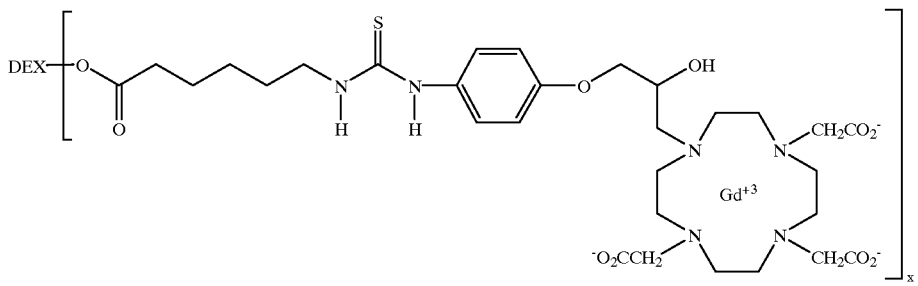

wherein x is at least 3.

29. A pharmaceutical agent having the formula

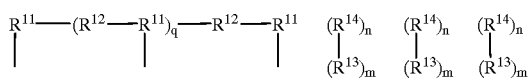

in which:

$R^{11}$ is a polysaccharide which is non-toxic and non-antigenic;

$R^{12}$ is a member selected from the group consisting C(O)—O and O—C(O), such that at least 10% of all $R^{12}$ groups are degraded in plasma after 24 hours;

$R^{13}$ is a complex of a ligand and a paramagnetic metal cation capable of altering contrast in magnetic resonance imaging;

$R^{14}$ is a spacer group which includes at least four atoms bonded together adjoining $R^{11}$ to $R^{13}$;

n is at least 1;

m is at least 1; and q is an integer from 0 to 5.

30. The agent according to claim 29, wherein $R^{12}$ is such that at least 35% of said linking groups are degraded in plasma after 24 hours.

31. The agent according to claim 29, wherein $R^{14}$ is poly(ethyleneglycol).

* * * * *

UNITED STATES PATENT AND TRADEMARK OFFICE
CERTIFICATE OF CORRECTION

PATENT NO. : 6,312,664 B1
DATED : November 6, 2001
INVENTOR(S) : Robert C. Brasch et al.

It is certified that error appears in the above-identified patent and that said Letters Patent is hereby corrected as shown below:

Column 21,
Line 34, kindly replace "u is2to 10." with -- u is 2 to 10. --

Column 23,
Lines 22-24, kindly replace
"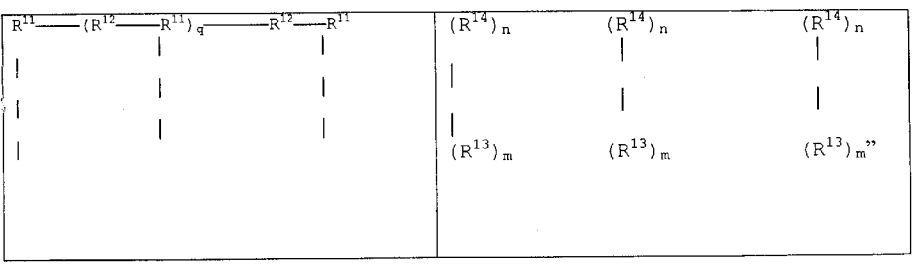"

with -- 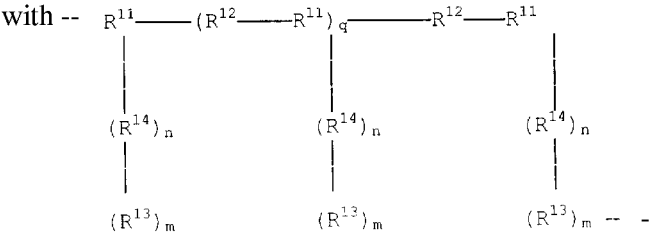 --

Signed and Sealed this

Thirteenth Day of July, 2004

JON W. DUDAS
*Acting Director of the United States Patent and Trademark Office*